United States Patent [19]

Albery et al.

[11] Patent Number: 4,891,102
[45] Date of Patent: Jan. 2, 1990

[54] METHOD OF DETERMINING CARBON DIOXIDE IN THE PRESENCE OF OXYGEN

[75] Inventors: Wyndham J. Albery; Anthony J. M. Coombs, both of London, England; Humphrey J. J. Drummond, Perth, Scotland; Clive Hahn, Radley, England

[73] Assignee: National Research Development Corporation, London, United Kingdom

[21] Appl. No.: 41,636

[22] Filed: Apr. 23, 1987

Related U.S. Application Data

[63] Continuation of Ser. No. 873,453, Jun. 6, 1986, abandoned, which is a continuation of Ser. No. 730,209, May 3, 1985, abandoned.

[30] Foreign Application Priority Data

May 4, 1984 [GB] United Kingdom ................. 8411448

[51] Int. Cl.$^4$ ........................................... G01N 27/46
[52] U.S. Cl. ................................... 204/1 T; 204/402
[58] Field of Search ............. 204/1 T, 1 Y, 1 H, 1 K, 204/402, 415, 418, 431, 432

[56] References Cited

U.S. PATENT DOCUMENTS

| | | | |
|---|---|---|---|
| 3,556,950 | 1/1971 | Dahms | 204/1 T |
| 3,681,255 | 8/1972 | Wilfore | 204/1 T X |
| 3,905,888 | 9/1975 | Mindt et al. | 204/415 |
| 4,077,861 | 3/1978 | Lauer | 204/415 X |
| 4,169,779 | 10/1979 | Tataria et al. | 204/415 X |
| 4,366,033 | 12/1982 | Richter et al. | 204/406 X |
| 4,377,446 | 3/1983 | Albery | 204/415 X |
| 4,400,242 | 8/1983 | Albery et al. | 204/415 X |

Primary Examiner—Nam X. Nguyen
Attorney, Agent, or Firm—Cushman, Darby & Cushman

[57] ABSTRACT

A method of determining one gas in the presence of another, where the one gas is reactive with an electrochemical product of the other, comprises applying the gases to one side of a membrane permeable to the two gases, the other side of the membrane retaining a solvent for both gases and for the electrochemical product, applying, for the predetermined duration through a working electrode in contact with the solvent, a potential which electrolyses (e.g. reduces) the (dissolved) other gas to form the said electrochemical product, applying, through the working electrode, a potential for reconverting the product to the dissolved gas, measuring, at a predetermined instant or integrated over a predetermined time slot, the current flowing at the reconversion potential, and, from the amount by which the measured current (or integrated current, i.e. charge) falls short of the current when the said one gas is absent, determining the concentration of the said one gas.

Optionally, the said other gas is also determined, by measuring the current flowing at the first potential.

The one gas may be carbon dioxide. The other gas may be oxygen. The solvent may be dimethylsulphoxide.

7 Claims, 2 Drawing Sheets

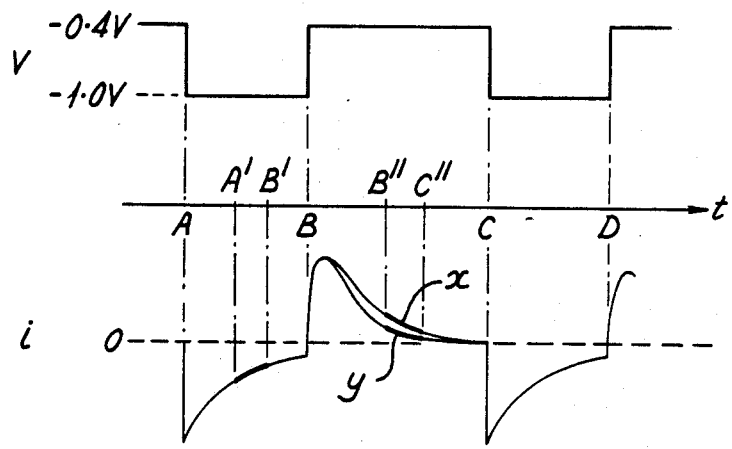

METHOD OF DETERMINING CARBON DIOXIDE IN THE PRESENCE OF OXYGEN

This is a continuation of application Ser. No. 873,453, filed June 6, 1986, which was abandoned upon the filing hereof and which was a continuation of Ser. No. 730,209 filed May 3, 1985, now abandoned.

This invention relates to a gas sensor which can determine one gas in the presence of another, where the one gas is reactive with an electrochemical product of the other, such as carbon dioxide in the presence of oxygen. For medical purposes it is often desirable to analyse exhaled breath, which still contains oxygen, for its carbon dioxide content, and also blood for its $CO_2$ tension.

According to the present invention, a gas sensor for determining one gas in the presence of another, where the one gas is reactive with an electrochemical product of the other, comprises a membrane permeable to the two gases, a solvent retained by the membrane for both gases and for the electrochemical product, a working electrode and a counter electrode in contact with the solvent, means for applying to the working electrode in sequence a potential for electrolysing (e.g. reducing) the said other gas to form the said electrochemical product for a predetermined duration and, after an optional but non-preferred rest period, a potential for reconverting the product to the gas, and means for measuring the current flowing at the reconversion potential and optionally also at the first potential. A reference electrode may be present, in contact with the solvent, to assist in monitoring the applied potentials.

Also according to the invention, a method of determining one gas in the presence of another, where the one gas is reactive with an electrochemical product of the other, comprises
- applying the gases to one side of a membrane permeable to the two gases, the other side of the membrane retaining a solvent for both gases and for the electrochemical product,
- applying, for a predetermined duration through a working electrode in contact with the solvent, a potential which electrolyses (e.g. reduces) the (dissolved) other gas to form the said electrochemical product,
- applying, through the working electrode, a potential for reconverting the product to the dissolved gas,
- measuring, at a predetermined instant or integrated over a predetermined time slot, the current flowing at the reconversion potential, and,
- from the amount by which the measured current (or integrated current, i.e. charge) falls short of the current when the said one gas is absent, determining the concentration of the said one gas.

Optionally, the said other gas is also determined, by measuring the current flowing at the first potential.

The one gas may be carbon dioxide. The other gas may be oxygen. The solvent may be dimethylsulphoxide. (Where the said other gas is oxygen, the solvent is preferably not propylene carbonate since this is more reactive with the electrochemical reduction product of oxygen.) The working electrode may be gold and the counterelectrode may be platinum. The reference electrode may be silver/silver chloride.

After the first potential has been applied for its predetermined duration, with the other gas (let us say oxygen) at a fixed concentration on the gas side of the membrane, a fixed quantity of electrolytically reduced oxygen, that is superoxide product $O_2{}^{\cdot-}$, is formed, In the absence of a gas reactive with this, the reconversion potential quantitatively oxidises some of the superoxide back to oxygen, passing a current which can be measured. However, if such a reactive gas (let us say carbon dioxide) is present, this will (much more rapidly) react with superoxide to form a product until all the carbon dioxide is used up, i.e. the superoxide 'titrates' the carbon dioxide. The reconversion potential will then oxidise only a predictable fraction of the remaining superoxide, passing only a correspondingly smaller current; the difference in currents or charges reveals the amount of carbon dioxide originally present. Where there is nil reconversion current, all the superoxide is consumed by the carbon dioxide, in other words the proportion of carbon dioxide in relation to the oxygen is too high to be measured by this technique with the parameters in use, and such steps may be taken as lengthening the said predetermined duration (of oxygen reduction) relative to the other steps.

The invention will now be described by way of example with reference to the accompanying drawings, in which.

Figure 1:
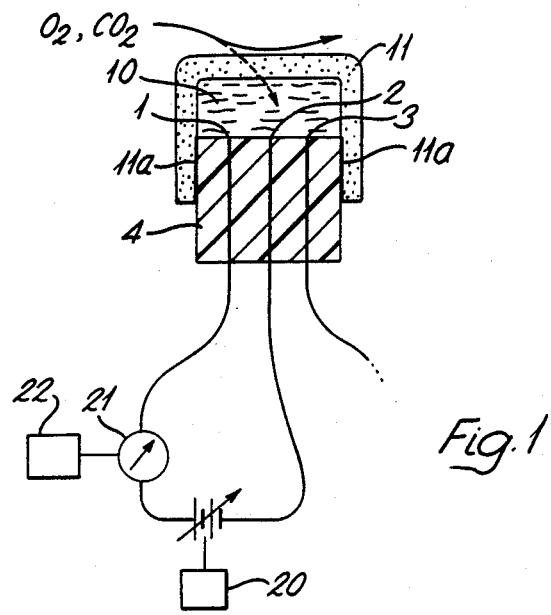
FIG. 1 shows a gas sensor according to the invention.

In FIG. 1, three electrodes 1, 2 and 3 are held in an inert insulating block 4. The electrodes are bathed in about 0.1 ml dimethylsulphoxide (DMSO) 10 which is held in place by a membrane 11 sealed to the block 4 at 11a. The membrane 11 is 10 microns thick and is permeable to gaseous oxygen and carbon dioxide, which are allowed to contact the outside of the membrane.

The electrode 1 is a working electrode, of gold. The electrode 2 is a counter electrode, of platinum. Although not shown as such, it may be annular, forming a ring around the working electrode 1. The electrode 3 is a silver/silver chloride reference electrode.

A control box 20 is programmed to apply a potential to the working electrode 1 varying according to a desired preset sequence. The current flowing is measured by an ammeter 21 whose output is interpreted by an indicator 22.

Figure 2:
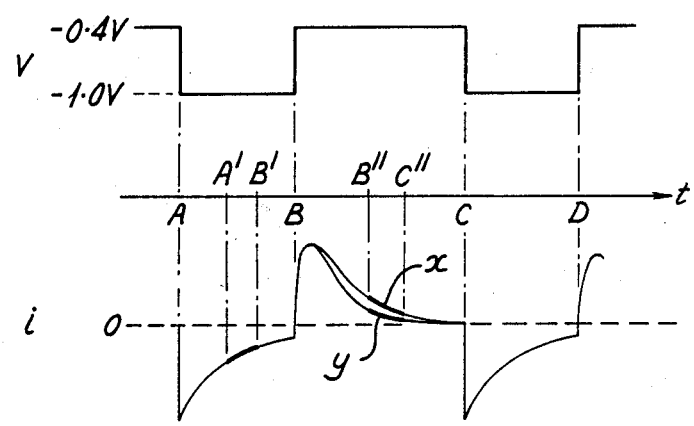
FIG. 2 shows a voltage and current-time traces given by the gas sensor in operation.

In use, oxygen of the expected background concentration (e.g. 15-20%), with no carbon dioxide, is passed over the membrane 11. As shown in FIG. 2, the control box 20 applies a voltage V (with respect to the Ag/AgCl reference electrode 3) to the working electrode 1 of −0.4V until instant A, then −1.0V until instant B, then −0.4V unitl instant C, then −1.0V until instant D, then −0.4V and so on. Durations AB and CD are 10 milliseconds each, and duration BC is 100 milliseconds. Alternatively AB and CD could be 50 ms and BC 200 ms. During AB and CD, the following reaction takes place at the working electrode 1:

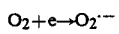

The quantity of product is directly deducible from the total current, i, which flows, and deducible by calibration and comparison from a 'spot' current reading at some fixed instant after A, such as A', or from a short time-integrated current determination over A'B', A' being a fixed instant after A'. The concentration of dissolved oxygen available for such reduction in the DMSO is, of course, proportional to its partial pressure in the ambient gas. For greater reliability, integrated current readings may be taken by the ammeter 21 additionally over one or several corresponding time intervals C'D' (not shown) and (if several) an overall average taken; even if an average is taken over 20 cycles, this will still take under 2½ seconds. The indicator 22 'learns' that current or charge represents what oxygen concentration in the gas.

The $O_2{}^{\cdot-}$ (superoxide) ion is stable in DMSO over short times.

During BC, the following reaction now occurs at the working electrode 1:

$$O_2{}^{\cdot-} \rightarrow O_2 + e$$

The rate of reaction tends to zero as all the $O_2{}^{\cdot-}$ becomes reconverted to oxygen. The current registered at the ammeter 21 is curve x, and the indicator 22 is 'taught' that curve x represents nil carbon dioxide at the oxygen concentration which it has already deduced.

Now carbon dioxide, say at a volume concentration of 5%, is admitted to the gas.

The current during AB and CD is predictable assuming the oxygen concentration remains constant. However, as the $O_2{}^{\cdot-}$ is produced on the working electrode 1, the following reaction takes place in the liquid DMSO 10:

$$O_2{}^{\cdot-} + CO_2 \rightarrow product$$

The working electrode 1 is switched to the reconversion potential (already described) and the following electrode reaction takes place:

$$O_2{}^{\cdot-} \rightarrow O_2 + e$$

The quantity of superoxide remaining after the (homogeneous) reaction with $CO_2$, for reconversion at the working electrode 1, is lessened, in direct proportion to the carbon dioxide concentration. This fact is reflected in the current registered at the ammeter 21, which is now curve y. The indicator 22 is 'taught' that curve y represents a 5% concentration of carbon dioxide at that oxygen concentration. Hence, for that cell operating under those conditions, the indicator can show the oxygen and the carbon dioxide concentrations in any other gas mixture (except, as previously explained, for mixtures containing more than a certain portion of carbon dioxide in relation to the oxygen, an unlikely mixture in medical applications).

Figure 3:
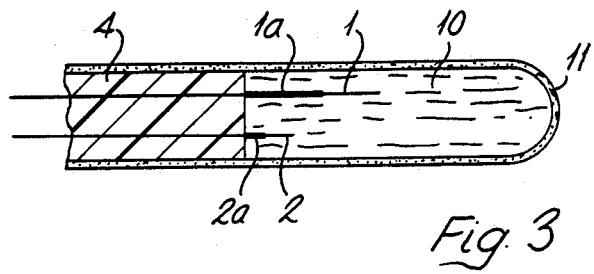
FIGS. 3, 4 and 5 show alternative designs of gas sensor according to the invention, more suitable for in-vivo blood $CO_2$ measurements.
Figure 4:
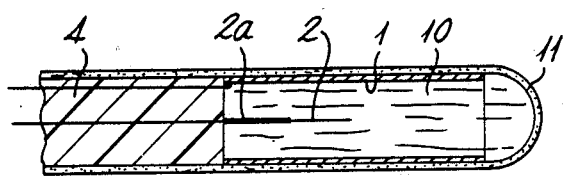
Figure 5:
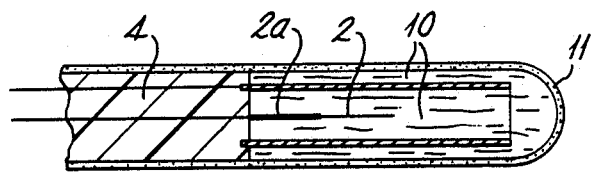

FIGS. 3, 4 and 5 show alternative designs of gas sensors, all working on the same electrochemical principles as the sensor of FIG. 1. The same reference numerals are used for corresponding components. FIGS. 3 to 5 are not to scale, as they represent in vivo sensors for analysing blood gas; for this purpose, a length of the illustrated part of about 100 mm and a diameter of two-thirds of 1 mm are suitable.

The working electrode 1, the cathode for reducing oxygen, is of gold, silver or platinum, partly protected by a PTFE insulating sleeve 1a (FIG. 3); in the case of FIG. 4, the working electrode 1 is a metallised layer formed on the inside of the cylindrical part of the membrane 11 (described later); in the case of FIG. 5, the cathode 1 is a hollow silver cylinder separated from the PTFE membrane 11 by a thin layer of dimethylsulphoxide 10. The cylindrical cathode 1 in FIGS. 4 and 5 could be foreshortened to form a ring instead.

The anode 2 (the counter electrode) is of silver, partly protected by a PTFE insulating sleeve 2a.

The PTFE membrane 11 is bathed in body fluid, and dissolved oxygen and carbon dioxide diffuse through it into the dimethylsulphoxide 10.

We claim:

1. A method of determining a first gas in the presence of a second gas, provided that the two gases fall into a class such that a product produced by the second gas at an electrode in a liquid electrolyte upon application of an electrical potential to the electrode is reactive with said first gas, the method comprising the steps of:

(a) applying the second gas by itself in a known concentration to one side of a membrane permeable to the two gases, the other side of the membrane retaining a solvent for both gases and for said product, (b) applying, for a predetermined duration through a working electrode in contact with the solvent, a potential which electrolyses the dissolved second gas to form said product produced at the working electrode when the potential is applied, (c) during the application of the electrolysing potential of step (b) measuring or integrating over a predetermined time slot the current flowing during step (b), (d) applying, through the working electrode, a reconversion potential which, by reversing the electrolysis of step (b), reconverts the product to the gas, (e) during the application of the reconversion potential, measuring or integrating over a predetermined time slot the current flowing during step (d), (f) applying the second gas in the known concentration of step (a) with the first gas in a known concentration to the said side of the said membrane, (g) repeating step (b), (h) repeating step (d), (i) repeating step (e), (j) subtracting the current measured in step (i) from the current measured in step (e) and recording the difference as characteristic of the known concentration of the first gas applied in step (f), (k) applying the gases to be determined to the said side of the said membrane, (l) applying, for said predetermined duration through said working electrode, the electrolysing potential of step (b) to form said product, (m) during the application of the electrolysing potential of step (l) measuring or integrating over a predetermined time slot the current flowing during step (l), (n) determining by comparison of the respective currents measured during steps (c) and (m) the concentration of the second gas present during step (k) in relation to the known concentration thereof applied during step (a), (o) applying through the working electrode, the reconversion potential of step (d) which reconverts the product to the gas, (p) during the application in step (o) of the reconversion potential, measuring or integrating over the predetermined time slot the current flowing during step (o), (q) subtracting the current measured in step (p) from the current that would have been expected in step (o) if the first gas had been absent, and (r) determining by comparison of the respective differences found in the substractions of steps (j) and (q) the concentration of the first gas present during step (k) in relation to the known concentration thereof applied during step (f).

2. A method according to claim 1, wherein the first applied potential reduces the dissolved other gas.

3. A method according to claim 1 wherein the first gas is carbon dioxide.

4. A method according to claim 3, wherein the second gas is oxygen.

5. A method according to claim 1, wherein the solvent is dimethylsulphoxide.

6. A method for determining the concentration of one gas, in samples of a gas mixture containing that one gas and another gas, in an instance in which said one gas is reactive with an electrochemical product of said other gas, said method comprising:

(a) providing a sensor which includes a two-sided membrane which is permeable to both said one gas and said other gas, this membrane having retained thereon and in communication therewith on one side thereof of a body of solvent which is capable of dissolving said one gas, said other gas and said electrochemical product, a working electrode and a counter-electrode in contact with said body of solvent at spaced sites, and a controllable source of electrical current arranged to be applied to said electrodes externally of said body of solvent in order, at selected times of selected duration, to cause electrochemical action to take place in said body of solvent;

(b) passing a reference gas containing a known concentration of said other gas, this known concentration being within a range of concentration expected for samples of said gas mixture, but including none of said one gas, over the other side of said membrane so that an amount of said other gas becomes dissolved in said solvent producing a concentration therein which is proportional to the partial pressure of said other gas in said reference gas;

(c) operating said controllable source of electrical current to apply across said electrodes during at least one first time period of predetermined duration an electrical potential which is sufficient to cause electrochemical conversion of said other gas to said electrochemical product in said body of solvent;

(d) measuring current flowing between said electrodes through said body of solvent during at least one of said first time periods throughout a first time interval within the respective said first time period, such interval being at least an instant in duration;

(e) operating said controllable source of electrical current to apply across said electrodes during at least one second time period of predetermined duration an electrical potential which is sufficient to cause or permit electrochemical reconversion of at least a predictable fraction of remaining said electrochemical product in said body of solvent to said other gas;

(f) measuring current flowing between said electrodes through said body of solvent during at least one of said second time periods throughout a second time interval within the respective said second time period, such interval being at least an instant in duration;

(g) passing a reference gas containing a known concentration of said other gas and a known concentration of said one gas over said other side of said membrane so that an amount of said other gas, and an amount of said one gas each become dissolved in said body of solvent producing concentrations therein which are respectively proportional to the partial pressures of said other gas and said one gas in this reference gas;

(h) repeating steps (c), (e) and (f) in respect to the body of solvent having said amounts of said other and one gases dissolved therein resulting from conducting step (g);

(i) obtaining by differencing the flowing currents measured in steps (f) and (h) a characteristic current flow effect of said known concentration of said one gas;

(j) from said measuring conducted in (d) and said differencing conducted in (i), at least one of extrapolated and repeated for different known concentrations of said one gas and said other gas, developing plots of characteristic current flow to be expected when conducting step (d) in respect to a sample of gas mixture containing an unknown concentration of said other gas which is within said expected range of concentration, and of characteristic current flow effect to be expected when conducting step (i) in respect to a sample of gas mixture containing an unknown concentration of said other gas which is within said expected range of concentration and an unknown concentration of said one gas which is no more than an amount sufficient to completely consume any of said electrochemical product in such sample by the end of the respective said at least one second time period;

(k) passing a sample of said gas mixture containing a concentration of said other gas within said expected range of concentration, and an unknown concentration of said one gas over said other side of said membrane so that an amount of said other gas and an amount of said one gas each becomes dissolved in said body of solvent producing concentrations therein which are respectively porportional to the partial pressures of said other gas and said one gas in this sample of said gas mixture;

(l) repeating steps (c), (d), (e), (f), (h) and (i) in respect to the body of solvent having said amounts of said other and said one gases dissolved therein resulting from conducting step (k); and (m) ascertaining from at least one of the current flowing as measured when repeating step (d) in step (l), and the current flow difference as measured when repeating step (i) in step (l), by reference to at least one of said plots developed in step (j), at least one of the concentration of said other gas and said other gas in said sample of said gas mixture.

7. The method of claim 6, wherein:
said other gas is oxygen and said one gas is carbon dioxide.